United States Patent
König et al.

(10) Patent No.: US 6,291,630 B1
(45) Date of Patent: Sep. 18, 2001

(54) METHOD FOR PRODUCING A LIQUID FORMULATION OF TETRAPHENYLPHOSPHONIUM PHENOLATE

(75) Inventors: Annett König; Michael Prein, both of Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/623,635

(22) PCT Filed: Mar. 1, 1999

(86) PCT No.: PCT/EP99/01330

§ 371 Date: Sep. 6, 2000

§ 102(e) Date: Sep. 6, 2000

(87) PCT Pub. No.: WO99/46315

PCT Pub. Date: Sep. 16, 1999

(30) Foreign Application Priority Data

Mar. 12, 1998 (DE) .............................................. 198 10 745

(51) Int. Cl.[7] .................................................. C08G 64/00
(52) U.S. Cl. .............................................................. 528/196
(58) Field of Search ..................................... 528/196, 198

(56) References Cited

U.S. PATENT DOCUMENTS

| 3,022,272 | 2/1962 | Schnell et al. | 528/196 |
| 3,442,854 | 5/1969 | Curtius | 528/196 |
| 4,302,574 | 11/1981 | Doorakian | 528/89 |
| 5,340,905 | 8/1994 | Kühling et al. | 528/199 |
| 5,399,659 | 3/1995 | Kühling et al. | 528/199 |

FOREIGN PATENT DOCUMENTS

| 1031512 | 6/1958 | (DE) . |
| 0798329 | 10/1997 | (EP) . |
| 0826692 | 3/1998 | (EP) . |
| 9900395 | 1/1999 | (WO) . |

OTHER PUBLICATIONS

Polymer Reviews, vol. 9, (month unavailable), 1964, pp. 44–51, Hermann Schnell, "Chemistry And Physics of Polycarbonates".

Liebigs Ann. Chem., vol. 634, (month unavailable), 1960, p. 1, von Hellmut Hoffmann, "Zur Kinetick Der Alkalischen Spaltung Quartärer Phosphoniumsalze".

J. Org. Chem., 32, (month unavailable), 1967, pp. 1060–1063, H. R. Hays, et al, "Reaction of Tetraalkylphosphoniumn Salts with Anhydrous Sodium Hydroxide".

Primary Examiner—Terressa M. Boykin
(74) Attorney, Agent, or Firm—Joseph C. Gil; Aron Preis

(57) ABSTRACT

A catalyst formulation that is liquid at room temperature and that comprise tetraphenylphosphonium phenolate and phenol is disclosed. The catalyst formulation is suitable as a transesterification catalyst and most especially in the preparation of thermoplastic solvent-free polycarbonates.

4 Claims, No Drawings

METHOD FOR PRODUCING A LIQUID FORMULATION OF TETRAPHENYLPHOSPHONIUM PHENOLATE

The present invention relates to a catalyst formulation, which is liquid at room temperature, of tetraphenylphosphonium phenolate and phenol and the use thereof as a transesterification catalyst, in particular for the solvent-free preparation of thermoplastic polycarbonates.

The preparation of phosphonium phenolate is known from DE-OS 196 35 656 and German Patent Application P 197 27 351.3. It is known from U.S. Pat. No. 3,442,854, inter alia, that phosphonium phenolates, optionally co-using alkali metal/alkaline earth metal compounds, are particularly suitable as catalysts for esterification and for transesterification, in particular for the preparation of polycarbonates by the melt transesterification process. Since metering in the catalyst as a solid presents technical difficulties, it is desirable to meter in the catalyst in liquid form. For example, the catalyst can be dissolved in liquid phenol, i.e. at temperatures above 45° C., in general at approx. 60° C., and can be fed to the process as a solution. This requires a heated reservoir and therefore additional technical expenditure. It is furthermore known from J. Org. Chem. 32 (1967) 1060 that phosphonium phenolates are unstable to heat, so that thermal predamage, in particular by a long residence of the catalyst solution in the heated reservoir, cannot be ruled out. Metering from a mixture, which is liquid at room temperature, of phenol and water (90 wt. %: 10 wt. %) offers another possibility. A disadvantage here is that water is introduced into the process as an additional substance. Liebigs Ann. Chem. vol. 634 (1960) 1 moreover describes the alkaline decomposition of quaternary phosphonium salts to triphenylphosphine oxide. According to our own investigations, small amounts of water at higyh temperatures also have the effect of cleavage of tetraphenylphosphonium phenolate (TPP-P) to triphenylphosphane oxide.

The object of the present invention was therefore to provide a simple possibility for liquid metering of tetraphenylphosphonium phenolate. It has now been found that a mixture of TPP-P, or the adduct of TPP-P with 2 molecules of phenol, called TPP-P*2PhOH in the following, with phenol at a composition of 28 to 45 wt. % TPP-P (or 40–65 wt. % TPP-P*2PhOH)-and correspondingly 72 to 55 wt. % (or 60 to 35 wt. %) phenol is liquid at room temperature. This allows addition of the catalyst in the liquid state without foreign substances or additives and without preliminary exposure of the catalyst to heat.

The liquid formulation obtained according to the invention of tetraphenylphosphonium phenolate can be used in a manner known per se as a catalyst for the preparation of aromatic polycarbonates (see, for example, U.S. Pat. No. 3,442,854). According to the melt transesterification process disclosed there, for example, aromatic polycarbonates are prepared from aromatic diphenols, carbonic acid diaryl esters and optionally branching agents and/or monophenols.

The phosphonium phenolates prepared according to the invention can be employed as transesterification catalysts in amounts of $10^{-1}$ mol to $10^{-8}$ mol, preferably in amounts of $10^{-3}$ mol to $10^{-7}$ mol, per mol of diphenol.

Further details of the melt transesterification process are described in the literature, (see, for example, Hermann Schnell, Chemistry and Physics of Polycarbonates, Polymer Reviews, vol. 9, 1964, pages 44 to 51, DE-AS 1 031 512, U.S. Pat. No. 3,022,272, U.S. Pat. No. 5,340,905 and U.S. Pat. No. 5 399 659).

The thermoplastic polycarbonates prepared with the liquid formulation according to the invention of TPP-P are solvent free, have a light intrinsic colour and are largely free from undesirable defects in the polycarbonate. In the context of the process according to the invention, largely free from undesirable defects in the polycarbonate means that the content of branching agents of the formula (I)

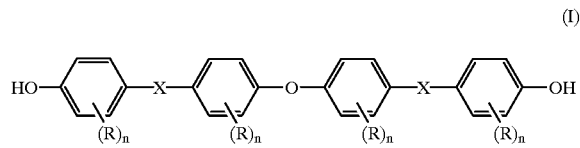

(I)

where

X=$C_1$–$C_9$-alkylidene or cycloalkylidene, S or a single bond and $(R)_n$=in each case independently of one another COOH, $CH_3$, Cl or Br, where several different $(R)_n$ can also occur on one phenyl ring n=0,1,2 or 3, in the polycarbonate does not exceed a value of 300 ppm according to total hydrolysis and HPLC determination.

EXAMPLES

Preparation of Various Pheno/TPP-P*2PhOH Mixtures

Phenol and TPP-P*2PhOH were weighed (total weight in each case 10 g) according to the compositions in table 1 into 20 ml rolled-edge bottles with a magnetic stirrer under an $N_2$ atmosphere and the bottles were closed with a septum. These bottles were clamped in an automatic shaking device and immersed in a heatable water bath. The temperature of the water bath was now increased stepwise (5° C./h) until the mixtures were in liquid form, and at the same time the shaking device ensured optimum mixing. After melting, the samples were taken out of the water bath and cooled to room temperature. Samples 4a, 5, 6 and 7 remained liquid, and the others formed a solid and a liquid phase or solidified. The melting temperatures ($T_{melt}$) of all the samples are summarised in table 1. These were determined by a procedure in which the samples which had been melted and cooled to room temperature were heated (5° C./h) by means of a water bath until they were liquid again.

TABLE 1

Composition of the catalyst formulations and their melting points

| Sample no. | PhOH [wt. %] | TPP-P [wt. %] | PhOH(g) | TPP-P*2PhOH(g) | $T_{melt}$ [° C.] |
|---|---|---|---|---|---|
| 1 | 100 | 0 | 10.00 | 0.00 | 42 |
| 2 | 85 | 15 | 7.86 | 2.14 | 39 |
| 3 | 80 | 20 | 7.14 | 2.86 | 34 |
| 4 | 75 | 25 | 6.43 | 3.57 | 28 |
| 4a | 72 | 28 | 6.00 | 4.00 | ≦23 |
| 5 | 70 | 30 | 5.71 | 4.29 | ≦15 |
| 6 | 60 | 40 | 4.29 | 5.71 | ≦15 |
| 7 | 55 | 45 | 3.57 | 6.43 | ≦18 |
| 8 | 50 | 50 | 2.86 | 7.14 | 52 |
| 9 | 40 | 60 | 1.43 | 8.57 | 90 |
| 10 | 30 | 70 | 0.00 | 10.00 | 143 |

Use Examples

Preparation of melt polycarbonate with a liquid TPP-P*2PhOH/PhOH catalyst solution

Example 1

114.15 g (0.500 mol) bisphenol A and 113.54 g (0.530 mol) diphenyl carbonate were weighed into a 500 ml three-necked flask with a stirrer, internal thermometer and Vigreux column (30 cm, metallized) with a bridge. The apparatus was freed from atmospheric oxygen by applying a vacuum and purging with nitrogen (3 times) and the mixture was heated up to 150° C. $4\times10^{-3}$ mol% tetraphenylphosphonium phenolate, based on the bisphenol A, in the form of liquid mixture no. 6 were then added and the phenol formed was distilled off under 100 mbar. At the same time, the temperature was increased up to 250° C. The vacuum was now improved stepwise down to 1 mbar and the temperature increased to 260° C. The temperature was then increased to 300° C., and the mixture was stirred under 0.1 mbar for 1.5 hours. A pale-coloured solvent-free polycarbonate with a relative solution viscosity of 1.260 (methylene chloride, 25° C., 5 g/l) was obtained. The content of branching agent of the formula (Ia) in the polycarbonate prepared was 25 ppm. The phenolic OH value of the polycarbonate was 70 ppm.

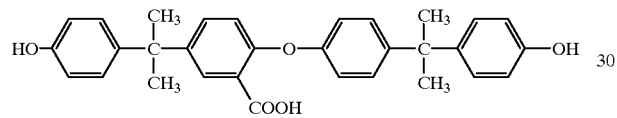

(Ia)

Example 2

As example 1, except with catalyst solution no. 5. A pale-coloured, solvent-free polycarbonate with a relative solution viscosity of 1.275 (methylene chloride, 25° C., 5 g/l) was obtained. The content of branching agent of the formula (Ia) in the polycarbonate prepared was 18 ppm. The phenolic OH value of the polycarbonate was 55 ppm.

What is claimed is:

1. Catalyst formulation which is liquid at room temperature, comprising 28 to 45 wt. % tetraphenylphosphonium phenolate and 72 to 55 wt. % phenol.

2. A method of using the Catalyst formulation of claim 1 comprising catalyzing a transesterification process.

3. The method of claim 2 wherein catalyst formulation is employed in an amount of 0.01 to 100,000 ppm.

4. A catalyzed transesterification process for the preparation of a thermoplastic, solvent-free polycarbonate resin comprising reacting at least one aromatic diphenol with at least one carbonic acid diaryl ester and optionally with a branching agent and/or monophenol, in the presence of $10^{-1}$ to $10^{-8}$ mol of the catalyst formulation of claim 1 per mol of diphenol.

* * * * *